(12) United States Patent
Berlin

(10) Patent No.: US 12,232,704 B2
(45) Date of Patent: Feb. 25, 2025

(54) ENDOSCOPIC INSTRUMENT FOR OPHTHALMIC SURGERY

(71) Applicant: Michael S. Berlin, Beverly Hills, CA (US)

(72) Inventor: Michael S. Berlin, Beverly Hills, CA (US)

( * ) Notice: Subject to any disclaimer, the term of this patent is extended or adjusted under 35 U.S.C. 154(b) by 0 days.

(21) Appl. No.: 17/907,474

(22) PCT Filed: Mar. 26, 2021

(86) PCT No.: PCT/US2021/024508
§ 371 (c)(1),
(2) Date: Sep. 27, 2022

(87) PCT Pub. No.: WO2021/202313
PCT Pub. Date: Oct. 7, 2021

(65) Prior Publication Data
US 2023/0118392 A1     Apr. 20, 2023

Related U.S. Application Data

(60) Provisional application No. 63/199,548, filed on Jan. 7, 2021, provisional application No. 63/002,578, filed on Mar. 31, 2020.

(51) Int. Cl.
*A61B 1/00* (2006.01)
*A61B 1/002* (2006.01)
(Continued)

(52) U.S. Cl.
CPC .......... *A61B 1/018* (2013.01); *A61B 1/00096* (2013.01); *A61B 1/002* (2013.01);
(Continued)

(58) Field of Classification Search
CPC .............................. A61B 1/055; A61B 1/0008
See application file for complete search history.

(56) References Cited

U.S. PATENT DOCUMENTS 4,607,622 A * 8/1986 Fritch ................... A61B 1/317
606/4
4,911,148 A   3/1990 Sosnowski
(Continued)

FOREIGN PATENT DOCUMENTS

FR      2653657      5/1991
GB      2561860     10/2018
(Continued)

OTHER PUBLICATIONS

"NanEye / NanEye Stereo, Miniature Camera Module," Datasheet—Public, v2-02, 38 pages (2018).
(Continued)

*Primary Examiner* — Timothy J Neal
(74) *Attorney, Agent, or Firm* — FisherBroyles, LLP; John K. Shimmick

(57) ABSTRACT

A surgical instrument comprises an elongate probe, in which the probe comprises an endoscope and a treatment channel. In some embodiments, the endoscope comprises a lens, in which the treatment channel extends through the distal end of the lens, which can facilitate alignment of the probe with a target tissue. In some embodiments, the treatment channel and the endoscope may comprise a co-axial configuration, which can decrease parallax when a user views the distal end of the working channel and target tissue beyond the distal end. Alternatively, the probe may comprise lenses arranged to provide stereoscopic vision of the end of the probe. The treatment channel may comprise an optical fiber to deliver light energy or a working channel. The treatment channel may comprise a housing such as a tube extending from the endoscope, in which the endoscope is configured to image the end of the treatment channel.

22 Claims, 7 Drawing Sheets

(51) Int. Cl.
*A61B 1/018* (2006.01)
*A61F 9/007* (2006.01)
*A61F 9/008* (2006.01)
*A61B 1/313* (2006.01)
*A61B 18/00* (2006.01)

(52) U.S. Cl.
CPC .......... *A61F 9/00781* (2013.01); *A61F 9/008* (2013.01); *A61B 1/313* (2013.01); *A61B 2018/00982* (2013.01)

(56) References Cited

U.S. PATENT DOCUMENTS

| | | | |
|---|---|---|---|
| 5,361,166 A * | 11/1994 | Atkinson | A61B 1/002 |
| | | | 359/654 |
| 5,693,003 A | 12/1997 | Woelfelschneider | |
| 6,296,608 B1 * | 10/2001 | Daniels | A61B 17/22 |
| | | | 600/478 |
| 6,764,439 B2 | 7/2004 | Schaaf | |
| 8,230,866 B2 | 7/2012 | Hauger | |
| 9,510,973 B2 | 12/2016 | Wardle | |
| 9,579,234 B2 | 2/2017 | Wardle | |
| 9,820,883 B2 | 11/2017 | Berlin | |
| 9,826,900 B2 | 11/2017 | Heeren | |
| 10,064,757 B2 | 9/2018 | Berlin | |
| 10,188,275 B2 | 1/2019 | Sonnenschein | |
| 10,285,856 B2 | 5/2019 | Tu | |
| 10,363,168 B2 | 7/2019 | Schieber | |
| 10,517,760 B2 | 12/2019 | Berlin | |
| 10,709,547 B2 | 7/2020 | Schieber | |
| 11,185,443 B2 | 5/2021 | Berlin | |
| 11,045,355 B2 | 6/2021 | Ianchulev | |
| 11,058,582 B2 | 7/2021 | Berlin | |
| 11,071,647 B2 | 7/2021 | Berlin | |
| 11,185,444 B1 | 11/2021 | Berlin | |
| 11,191,670 B1 | 11/2021 | Berlin | |
| 11,197,779 B2 | 11/2021 | Van Meter | |
| 11,197,780 B2 | 12/2021 | Haffner | |
| 11,318,045 B2 | 5/2022 | Berlin | |
| 11,318,046 B2 | 5/2022 | Berlin | |
| 11,318,047 B2 | 5/2022 | Berlin | |
| 11,583,443 B2 | 2/2023 | Berlin | |
| 11,583,444 B2 | 2/2023 | Berlin | |
| 11,590,024 B2 | 2/2023 | Berlin | |
| 11,723,805 B2 | 8/2023 | Berlin | |
| 11,759,357 B2 | 9/2023 | Berlin | |
| 11,850,186 B2 | 12/2023 | Berlin | |
| 12,048,648 B2 | 7/2024 | Berlin | |
| 2001/0053873 A1 * | 12/2001 | Schaaf | A61F 9/00781 |
| | | | 600/166 |
| 2002/0013572 A1 | 1/2002 | Berlin | |
| 2002/0188285 A1 | 12/2002 | Brown | |
| 2003/0045780 A1 * | 3/2003 | Utsui | A61B 1/0638 |
| | | | 600/104 |
| 2003/0097151 A1 | 5/2003 | Smedley | |
| 2003/0229303 A1 | 12/2003 | Haffner | |
| 2004/0024345 A1 | 2/2004 | Gharib | |
| 2005/0250788 A1 | 11/2005 | Tu | |
| 2005/0272977 A1 * | 12/2005 | Saadat | A61B 1/00183 |
| | | | 600/114 |
| 2006/0041193 A1 | 2/2006 | Wright | |
| 2006/0173397 A1 | 8/2006 | Tu | |
| 2007/0118014 A1 | 5/2007 | Fuerst | |
| 2008/0082078 A1 | 4/2008 | Berlin | |
| 2009/0163898 A1 | 6/2009 | Gertner | |
| 2009/0292170 A1 | 11/2009 | Boebel | |
| 2010/0179652 A1 | 7/2010 | Yamamoto | |
| 2010/0204609 A1 | 8/2010 | Worth | |
| 2010/0286475 A1 * | 11/2010 | Robertson | A61B 1/00188 |
| | | | 600/109 |
| 2011/0118611 A1 | 5/2011 | Luciano | |
| 2011/0282190 A1 | 11/2011 | Caffey | |
| 2012/0283557 A1 | 11/2012 | Berlin | |
| 2012/0300032 A1 * | 11/2012 | Ookoba | A61B 1/018 |
| | | | 348/45 |
| 2013/0103011 A1 | 4/2013 | Grant | |
| 2014/0275763 A1 | 9/2014 | King | |
| 2014/0288485 A1 | 9/2014 | Berlin | |
| 2014/0336465 A1 | 11/2014 | Demers | |
| 2015/0025320 A1 | 1/2015 | Rogers | |
| 2016/0089032 A1 | 3/2016 | Toriyama | |
| 2016/0143778 A1 | 5/2016 | Aljuri | |
| 2016/0262606 A1 | 9/2016 | Mosaed | |
| 2017/0042736 A9 | 2/2017 | Berlin | |
| 2017/0202708 A1 | 7/2017 | Berlin | |
| 2018/0235462 A1 | 8/2018 | Gooi | |
| 2018/0360310 A1 | 12/2018 | Berlin | |
| 2018/0369017 A1 | 12/2018 | Schieber | |
| 2019/0000561 A1 | 1/2019 | Decker | |
| 2019/0117459 A1 | 4/2019 | Berlin | |
| 2019/0159662 A1 | 5/2019 | Papas | |
| 2020/0085620 A1 | 3/2020 | Euteneuer | |
| 2020/0179171 A1 | 6/2020 | Crimaldi | |
| 2020/0193600 A1 | 6/2020 | Shameli | |
| 2020/0197221 A1 | 6/2020 | Schieber | |
| 2020/0222238 A1 | 7/2020 | Schieber | |
| 2021/0000979 A1 | 1/2021 | Coroneo | |
| 2021/0030590 A1 | 2/2021 | Blanda | |
| 2021/0154449 A1 | 5/2021 | Haffner | |
| 2021/0330499 A1 | 10/2021 | Wardle | |
| 2021/0361479 A1 | 11/2021 | Wardle | |
| 2021/0393110 A1 | 12/2021 | Ohse | |
| 2022/0287879 A1 | 9/2022 | Berlin | |
| 2022/0287880 A1 | 9/2022 | Berlin | |
| 2022/0287881 A1 | 9/2022 | Berlin | |
| 2023/0157875 A1 | 5/2023 | Berlin | |

FOREIGN PATENT DOCUMENTS

| | | |
|---|---|---|
| JP | 2017099757 | 6/2017 |
| WO | 2000067687 | 11/2000 |
| WO | 2001089437 | 11/2001 |
| WO | 2005094665 | 10/2005 |
| WO | 2017094243 | 6/2017 |
| WO | 2018049246 | 3/2018 |
| WO | 2018232397 | 12/2018 |
| WO | 2020215062 | 10/2020 |
| WO | 2020215064 | 10/2020 |
| WO | 2020215066 | 10/2020 |
| WO | 2020215067 | 10/2020 |
| WO | 2020215068 | 10/2020 |
| WO | 2020215069 | 10/2020 |
| WO | 2020215071 | 10/2020 |
| WO | 2020215073 | 10/2020 |
| WO | 2021003304 | 1/2021 |
| WO | 2021055751 | 3/2021 |
| WO | 2021202313 | 10/2021 |

OTHER PUBLICATIONS

Bende, et al., "Fiberoptic Partial Coherence Interferometry (PCI): A Novel Approach to Locate Schlemm's Canal for MIGS Surgery," ARVO 2016 Poster.

Berlin, Michael S., et al. "Excimer Laser Trabeculostomy: An Effective Microinvasive Glaucoma Surgery Procedure for Open-Angle Glaucoma," 13 sheets (Dec. 19, 2013.

Berlin, Michael S., et al., "Chapter 16, Excimer Laser Trabeculostomy (ELT): An Effective MIGS Procedure for Open-Angle Glaucoma," New Concepts in Glaucoma Surgery Series: vol. 1, pp. 233-246, edited by John R. Samples and Ike Ahmed, Kugler Publications, Amsterdam, The Netherlands (2019).

Berlin, Michael S., et al., "Chapter 8, Excimer Laser Trabeculostomy (ELT): An Effective MIGS Procedure for Open-Angle Glaucoma," Surgical Innovations in Glaucoma, pp. 85-95 (2014). 2014.

Berlin, Michael S., et al., "Excimer Laser Trabeculostomy (ELT): An Effective MIGS Procedure for Open-Angle Glaucoma," J.R. Samples, I.I.K. Ahmed (eds.), Surgical Innovations in Glaucoma, Springer Science+Business Media New York , pp. 85-95 (2014).

Berlin, Michael S., et al., Chapter 16, "Excimer laser trabeculostomy (ELT): the laser-based MIGS procedure for open-angle glaucoma," New Concepts in Glaucoma Surgery Series: vol. 1, pp. 233-246 (2019).

(56) References Cited

OTHER PUBLICATIONS

Catalogue PolyDiagnost, 22 pages (Jul. 2018).
Durr, Georges M., et al., "Current review of Excimer laser Trabeculostomy," Eye and Vision, 7:24, 9 pages (2020).
FiberTech, FC304 User Manual (Rev. 1), U88045-E1, 3CMOS HD Camera FC-304, Endoscopic video camera, 49 pages (Oct. 2016).
FiberTech, FL-301 User Manual (Rev. 1) U88046-E1, 3LED Light Source FL-301, Endoscope Light Source (Externally Powered), 32 pages (Oct. 2016).
FiberTech, Solid Fiber Catheter AS-611 Instructions for Use (1st Ed.), Ophthalmic Endoscope, U88033-E, 12 pages, undated but to the best of undersigned attorney's belief and knowledge is believed to be prior to Jul. 1, 2019.
Fisher, Yale L., "A Disposable Ophthalmic Endoscopic System," Arch Ophthalmol, 112:984-986 (Jul. 1994).
FormLabs, "Creating Camera Lenses with Stereolithography," retrieved from https://formlabs.com/blog/creating-camera-lenses-with-stereolithography/, 14 pages (Jan. 5, 2021).
Francis, Brian A., et al., "Endoscopic ophthalmic surgery of the anterior segment," SciVerse ScienceDirect (2013), retrieved Jan. 18, 2022 from http://www.endooptiks.com/assets/francis-survey-endoscopic-ant-seg-surgery-aug-2013.pdf.
Funk, Jens, et al., "Trabecular meshwork ablation shows promise as alternative to invasive glaucoma surgery," retrieved Mar. 17, 21 from https://www.healio.com/news/ophthalmology/20120225/trabecular-meshwork-ablation-shows-promise-as-alternative-to-invasive-glaucoma-surgery, (Nov. 1, 2004).
Glaukos Corporation iStent inject Trabecular Micro-Bypass System, Directions for Use/Package Insert, P170043C iStent Inject IFU (Jun. 15, 2018).
Glaukos Corporation iStent Trabecular Micro-Bypass Stent, P080030c iStent Inject IFU, 23 pages (undated but believed to be prior to Jan. 28, 2021).
Hommayda, Sufian, et al., "The AIDA and the extra laser systems for excimer laser trabeculotomy proved comparalbe IOP lowering efficacy—12-month results," Int Ophthalmol 42:1507-1514 (2022).
International Search Report and Written Opinion for PCT/US2021/024508, 17 pages, Jul. 9, 2021.
Ivantis Hydrus Microstent Instructions for Use, P170034D Hydrus IFU, 21 pages (Aug. 2018).
Ivantis Hydrus Microstent Patient Information Brochure, P170034C Hydrus, 10 pages (Aug. 2018).
Jacobi, Philipp C., et al., "Perspectives in trabecular surgery," Eye 14:519-530 (2000).
Loewen, Nils A. and Schuman, Joel S., "There has to be a better way: evolution of internal filtration glaucoma surgeries," Br J Ophthalmol 97(10):1228-1229 (2013).
MLase AG, ExTra Operating Instructions, 703-FB 508237 Manual ExTra EN (Rev02), 37 pages (Apr. 2016).
MLaseAG, Specifications ExTra Laser for Glaucoma Treatment, 1 page (Jul. 13, 2012).
MLaseAG, Specifications FIDO Laser applicator for ExTra Laser System, 1 page (Jul. 13, 2012).
MLaseAG, Specifications FIDO laser applicator for ExTra Laser System, 1 page (Sep. 26, 2013).
Toteberg-Harms, M., et al., "Cataract Surgery combined with excimer laser trabeculotomy to lower intraocular pressure: effectiveness dependent on preoperative IOP," BMC Ophthalmology 13:24, 9 pages, http://www.biomedcentral.com/1471-2415/13/24 (2013).
Tui Laser AG, "Investigational Testing Authorization Application," 43 pages (Sep. 21, 2004).
TuiLaser AG, Bedienungsanleitung, AIDA, OM-100-GL/Version 2.2, 38 pages, English transation (Aug. 2005).
TuiLaser AG, Bedienungsanleitung, AIDA, OM-100-GL/Version 2.2, 38 pages, German version (Aug. 2005).

\* cited by examiner

ENDOSCOPIC INSTRUMENT FOR OPHTHALMIC SURGERY

RELATED APPLICATIONS

This application is a 371 national phase of PCT/US2021/024508, filed Mar. 26, 2021, published as WO 2021/202313 A1 on Oct. 7, 2021, and claims the benefit under 35 U.S.C. § 119(e) of U.S. Provisional Application No. 63/199,548 filed Jan. 7, 2021, and of U.S. Provisional Application No. 63/002,578, filed Mar. 31, 2020, both entitled "ENDOSCOPIC INSTRUMENT FOR OPHTHALMIC SURGERY," the disclosures of which are incorporated, in their entirety, by this reference.

The subject matter of this patent application is related to PCT/US2020/040558, filed on Jul. 1, 2020, published as WO/2021/003304 on Jan. 7, 2021, the disclosure of which is incorporated, in its entirety, by this reference.

BACKGROUND

Prior approaches to surgery such as ophthalmic surgery to treat glaucoma can be less than ideal in at least some respects. With some surgeries, viewing a target tissue such as Schlemm's canal can be more difficult than would be ideal. For example, with some glaucoma surgeries a lens such as a goniolens is used to view the angle of the eye. Although intraocular endoscopes have been proposed for use with ocular surgery, the prior endoscopic probes can be less than ideal in at least some respects and may be more complicated than would be ideal, and are not well suited for single use with a sterile probe.

SUMMARY

In some embodiments, a surgical instrument comprises an elongate probe, in which the probe comprises an endoscope and a treatment channel. In some embodiments, the endoscope comprises a lens, in which the treatment channel extends through the distal end of the lens, which can facilitate alignment of the probe with a target tissue beyond the probe. In some embodiments, the treatment channel and the endoscope may comprise a co-axial configuration, which can decrease parallax when a user views the distal end of the working channel and target tissue beyond the distal end. Alternatively, the endoscope may comprise lenses arranged to view the distal end of the working channel with parallax in order to provide stereoscopic vision of the distal end of the probe in relation to tissue, which can improve visualization and placement of the distal end in relation to tissue. The treatment channel may comprise one or more of an optical fiber to deliver light energy or a working channel to provide an implant, adjust an implant, or perform a procedure. In some embodiments, the endoscope comprises a rod, in which the treatment channel is located within the rod. The treatment channel may comprise a housing such as a tubular sheath extending from the endoscope, in which the endoscope is configured to image the endoscope near the distal end of the working channel. The endoscope may comprise a depth of field, in which the distal end of the housing of the treatment channel is located within a proximal portion of the depth of field in order to image tissue beyond the end of the treatment channel. In some embodiments, the treatment channel comprises an optical fiber at least partially enclosed in a housing such as a tube extending beyond a distal end of the endoscope. Alternatively, the treatment channel may comprise a working channel defined with a housing such as a tube extending beyond a distal end of the endoscope, in order to provide the implant, adjust the implant or perform a procedure.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed methods and apparatus are well suited for incorporation with many surgical procedures, such as glaucoma surgery retinal surgery, suprachoroidal surgery, vitreous surgery, orthopedic surgery, insertion of pharmacologic dispensing devices and therapeutic agents, vascular surgery, cardiac surgery, neurosurgery, urologic surgery, GI surgery, abdominal surgery, implant surgery, laser treatments, implants for glaucoma surgery, thermal and blade based trabecular meshwork surgery, and lasers for laser surgery to treat glaucoma such as excimer laser trabeculostomy ("ELT"). Although reference is made to a surgical handpiece, the presently disclosed methods and apparatus will find application in many fields.

Figure 1:
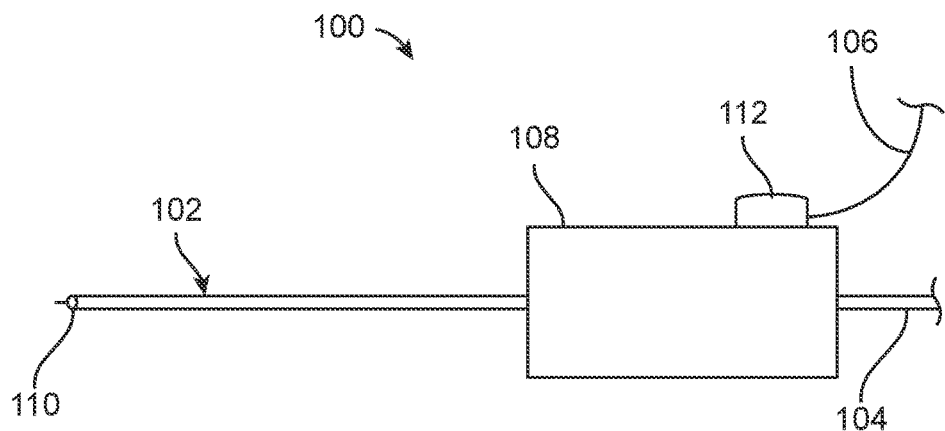
FIG. 1 shows a surgical probe comprising a treatment channel and an imaging channel, in accordance with some embodiments.

FIG. 1 shows a surgical instrument 100 comprising a surgical probe 102 comprising a treatment ("Tx") channel 104 and an imaging channel 106. The treatment channel 104 may be configured in many ways, and may comprise an optical fiber 402 to deliver light energy, or a working channel to provide therapy with an implant 506, such as to one or more of place, position, deliver, adjust or remove an implant 506, perform tissue manipulation, or perform a procedure, for example. In some embodiments, the surgical instrument 100 comprises a handpiece 108 coupled to the surgical probe 102 endoscope 202 (FIG. 2) and the treatment channel 104 for a surgeon to manipulate the distal end 110 and provide a treatment, such as a laser 222 treatment or an implant 506. The handpiece 108 can be configured in many ways, in order to provide controlled insertion, removal, manipulation, adjustment of the implant 506 and aiming of the laser 222 delivery channel, for example. The imaging channel 106 can be configured in many ways and may comprise an endoscope 202, for example. In some embodiments the endoscope 202 comprises a rod, a single optical fiber 402, or a plurality of optical fibers 402, arranged with respect to the treatment channel 104, such as around the treatment channel 104, in order to image the target tissue.

In some embodiments, the handpiece 108 of the probe 102 comprises one or more indicia of alignment with the distal end 110 of the probe, such as one or more tactile indicia of alignment. The one or more indicia of alignment can allow the user, e.g. the surgeon, to sense the rotation of the probe 102 about the elongate axis of the probe 102. The one or more tactile indicia of alignment may comprise one or more of a flat surface, a nub, bump, groove, intrusion, detent, finger receiving concavity, or other structure on the handpiece 108 aligned with a treatment structure on the distal end 110 of the probe 102. The treatment structure may comprise one or more of a bevel on a distal end of the probe 102, or an insertion direction of an implant 506, for example. This one or more tactile indicia of alignment can allow the surgeon to feel the alignment of the distal end 110 of the probe 102 based on the orientation of the proximal end of the probe 102 in order to facilitate alignment.

In some embodiments, the imaging channel 106 comprises an endoscope 202 configured to transmit an image of tissue near the distal end 110 of the probe to a sensor 112, such as an array sensor. The endoscope 202 can be configured in many ways, and may comprise an optically transmissive rod with an internal channel such as a bore. The rod may comprise any suitable optically transmissive material, such as a quartz, glass, fused silica, or plastic, for example. Alternatively or in combination, the endoscope 202 may comprise a plurality of optical fibers 402 located around the treatment channel 104, such as the optical fiber 402 or the working channel.

In some embodiments, the image sensor 112 is coupled to the endoscope 202 with a connector 204 (of FIG. 2), such that the image sensor 112 can be reused, and the endoscope 202 disposed of or sterilized for reuse, for example.

In some embodiments, the surgical probe 102 is used with external illumination, such as illumination from an operating microscope. Alternatively or in combination, the surgical probe 102 may comprise one or more illumination fibers. The one or more illumination fibers can be coupled to a light source to provide light to the treatment area near the tip of the probe.

Figure 2:
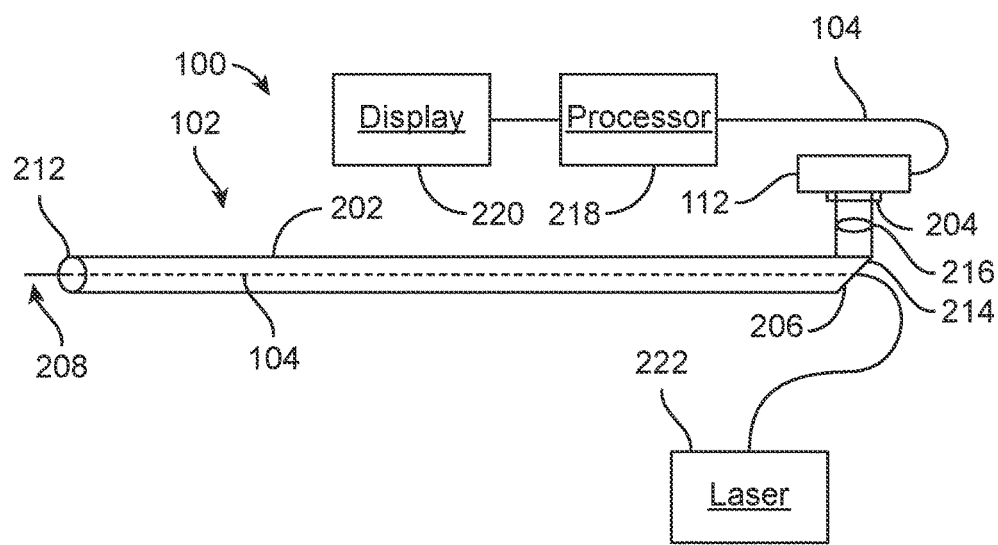
FIG. 2 shows a schematic of a probe as in FIG. 1, in which the surgical probe comprises a treatment channel extending within an endoscope, in which the endoscope comprises a mirror, in accordance with some embodiments.

FIG. 2 shows a schematic of a probe 102 as in FIG. 1, in which the surgical probe 102 comprises a treatment channel 104 extending within an endoscope 202, in which the endoscope 202 comprises a mirror 206. The surgical probe 102 comprises a treatment tip 208 configured to deliver treatment, and an endoscope 202 configured to image the target tissue. An endoscope tip 212 can be configured in many ways and may comprise a curved surface, such as a curved surface of a lens to image the target tissue. In some embodiments, the treatment tip 208 extends a distance beyond the endoscope tip 212. Alternatively, the treatment tip 208 and endoscope tip 212 may be located adjacent to each other.

The endoscope 202 may comprise a rod 302 (FIG. 3) with a treatment channel 104 extending along an interior of the rod 302. The endoscope 202 may comprise a housing located over the rod, for example. The housing may comprise a tubular sheath, which can be stiff or flexible, for example. The housing, e.g. the tubular sheath can be configured to retain at least a portion of the endoscope 202, for example if the portion of the endoscope 202, e.g. the rod, were to fracture. The mirror 206 may comprise a beveled proximal end 214 of the rod in which the proximal beveled end 214 of the rod is beveled at a suitable angle to reflect light toward the image sensor 112. The beveled surface can be coated to reflect light in order to increase the reflectivity of the surface, for example. The proximal beveled end 214 may comprise an opening through which the treatment channel 104 extends. The treatment channel 104 may comprise an optical fiber 402 or a working channel of the endoscope 202 extending through the proximal beveled end 214. In some embodiments, an optical fiber 402 extends through the proximal beveled end 214. Alternatively or in combination, a working channel such as a tube extends through the proximal beveled end 214.

The proximal beveled end 214 near the proximal end can be configured in many ways. In some embodiments, the beveled surface comprises a mirror 206 surface. Alternatively or in combination, the surface may comprise convex or concave mirrored surface 206, in order to allow the full sensor 112 to receive the image or to provide a suitable magnification.

In some embodiments, the image sensor 112 may be a sensor array 112 and may comprise any suitable sensor array 112, such as a CMOS or other sensor array 112 such as any of the sensors described herein, such as the sensor shown and described in relation to FIG. 1. In some embodiments, the sensor array 112 comprises an aperture that is sized and shaped to allow the treatment channel 104 to extend through the sensor array 112, which can allow the sensor array 112 to be optically coupled to the endoscope 202 without a mirror 206, for example. Alternatively or in combination, the sensor array 112 may comprise a plurality of sensors distributed around the treatment channel 104, such as an annular array of sensor elements distributed around the treatment channel 104.

The endoscope 202 may comprise one or more lenses 216 to from an image the target tissue region on the sensor array 112. The image sensor 112 array can be coupled to a processor 218 and a display 220 for a surgeon to view the target treatment site. The processor 218 can be configured to control one or more components of the system to deliver treatment, and can be coupled to a laser 222 for example.

In some embodiments, the treatment channel 104 comprises an optical fiber 402 extending from a proximal end of the probe, and the optical fiber 402 is configured to couple to a laser 222. The treatment channel 104 may be configured in many ways, and may comprise an optical fiber 402 to deliver light energy, or a working channel to provide therapy with an implant 506, such as to one or more of place, position, deliver, adjust or remove an implant 506, tissue manipulation, or perform a procedure, for example.

The surgical probe 102 can be configured in many ways, and may comprise a single use surgical probe 102 provided in a sterile package for single use. In some embodiments, the surgical probe 102 enclosed in the sterile package comprises the endoscope 202, the treatment channel 104 and the sensor array 112, in which the endoscope 202 comprises one or more connectors to connect to the display 220 and the treatment apparatus. In some embodiments, the surgical probe 102 enclosed in the sterile package comprises an electrical connector 204 to couple to a video input of a surgical system and an optical fiber 402 connector to couple to a source of treatment energy such as laser treatment energy. Alternatively, the surgical probe 102 enclosed in the sterile package comprises an implant 506 and an electrical connector 204 to couple to a video input of a display 220 or a processor 218. In some embodiments, the endoscope 202 comprises one or more imaging optical fibers 402 having a length sufficient to extend from the handpiece 108 to a detector placed in a console, e.g. a length of at least about 0.5 meters. In some embodiments, the treatment channel 104 comprises a treatment optical fiber 402, and the endoscope 202 comprises one or more imaging optical fibers 402, each having a length of at least about 0.5 meters.

Although reference is made to a single use disposable endoscope 202 comprising an image sensor 112, in some embodiments the image sensor 112 is coupled to the endoscope 202 with a connector 204, such that the image sensor 112 can be reused, and the endoscope 202 disposed of, for example.

The laser 222 may comprise any suitable source of laser 222 energy for delivery to the eye. In some embodiments, the laser 222 is configured to emit light energy within a wavelength from about 190 nm to about 2000 nm. The laser 222 may comprise any suitable laser, such one or more of a solid state laser, a gas laser, a pulsed laser, a fiber optic pulsed laser, a frequency mixing laser, a harmonic of a fundamental wavelength, such as a frequency quintupled alexandrite laser, an excimer laser, or an XeCl excimer laser emitting light at 308 nm, for example.

Figure 3:
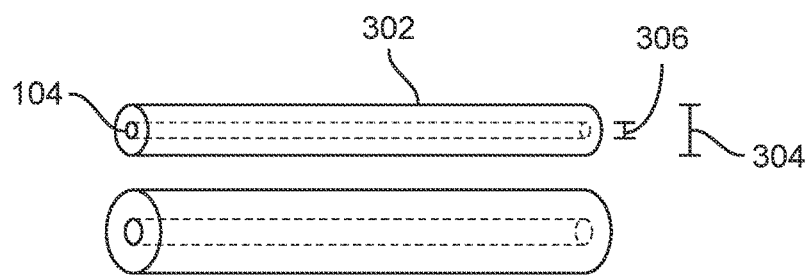
FIG. 3 shows a rod with an internal treatment channel, in accordance with some embodiments.

FIG. 3 shows a rod 302 with an internal treatment channel 104 suitable for use with an endoscope 202. The rod 302 may comprise any suitable outer diameter 304, such as a diameter within a range from about 0.5 mm to about 5 mm.

The internal treatment channel 104 may comprise any suitable diameter 306, such as within a range from about 0.1 mm to about 1 mm, optionally within a range from about 0.15 mm to about 0.3 mm for example.

Figure 4:
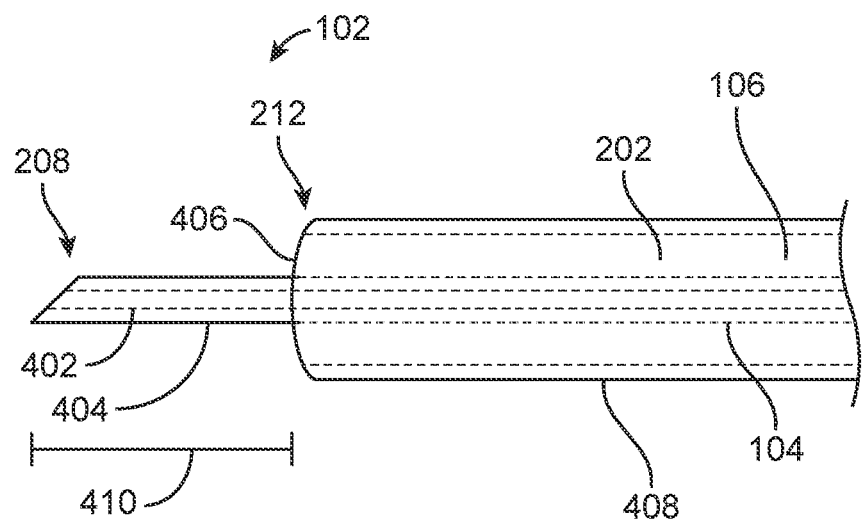
FIG. 4 shows a surgical probe comprising an endoscope and an optical fiber and housing extending along an interior of the endoscope, in accordance with some embodiments.

FIG. 4 shows a surgical probe 102 comprising an endoscope 202 and an optical fiber 402 and housing 404 extending along an interior of the endoscope 202. The housing 404 extending along the interior of the endoscope 202 can be configured in many ways, and may comprise a tubular sheath, for example. The sheath can be stiff or flexible, for example. The sheath can be configured to retain one or more components of the treatment channel 104, for example if a portion of the treatment channel 104, e.g. if the optical fiber 402 were to fracture. In some embodiments the sheath comprises a metal, such as stainless steel, although any suitable material can be used such as plastic, for example. The end of the endoscope 202 comprises a curved surface, which may comprise a surface of a lens 406. The endoscope 202 comprises a housing 408 that encloses the endoscope 202. The endoscope 202 may comprise a rod 302 with an inner channel 104 as described herein. The treatment channel 104 may comprise an optical fiber 402 with a housing 404 disposed over the optical fiber 402. The housing of the treatment channel 104 extends to a tip 208, with the optical fiber 402 located along an interior of the housing 404. In some embodiments, the optical fiber 402 and the optical fiber housing 404 comprise a beveled distal end 208. Alternatively, the end 208 may comprise a non-beveled surface. In some embodiments, the end of the treatment channel 104 comprising the housing and the optical fiber 402 is located a distance 410 from the end of the endoscope 202. The distance 410 can be any suitable distance and can be within a range from about 0 mm to about 10 mm, optionally within a range from about 1 mm to about 5 mm. In some embodiments, the distance 410 is dimensioned for the endoscope 202 to image the distal tip 208 of the treatment channel housing 404, and the endoscope 202 comprises a sufficient depth of field to image the tissue beyond the distal tip 208, for example within a range from 0.5 mm to 2 mm beyond the distal tip 208. Alternatively, the end of the optical fiber 402 and housing 404 can be located in close proximity to the curved surface of the endoscope 202.

In some embodiments, the treatment channel 104 extends beyond a distal end of an optical fiber 402 in order to illuminate a distal end 208 of the treatment channel 104 with light emitted from the distal end of the optical fiber 402. The endoscope 202 can be configured in many ways and may comprise one or more optical fibers 402 configured to illuminate the distal end and the tissue. In some embodiments, an imaging channel 106 of the endoscope 202 comprises the one or more optical fibers 402 to illuminate the distal end and the tissue.

In some embodiments, one or more of the imaging channel 106 or the treatment (Tx) channel 104 is used to transmit viewing light to the end of the probe 102. In some embodiments, light is transmitted along the imaging channel 106 to illuminate the end of the probe 102. In some embodiments, the treatment channel 104 comprises an optical fiber 402 as described herein, and visible light is transmitted along the optical fiber 402 to illuminate tissue near the end of the probe 102. In some embodiments, the illumination optical fiber 402 comprises a separate optical fiber 402 from the treatment channel 104 and the imaging channel 106 of the endoscope 202. In some embodiments, the treatment optical fiber or the imaging optical fiber comprises a cladding layer that is used to transmit light energy, for example with a dual cladding layer. The proximal end of the illumination optical fiber 402 can be coupled to a light source to provide light to the distal end of the probe as is known to one of ordinary skill in the art. In some embodiments, the treatment optical fiber 402 is coupled to a light source with a beam splitter, as described in U.S. Pat. No. 10,383,689, issued Aug. 20, 2019, entitled "Delivery system and method of use for the eye".

Figure 5:
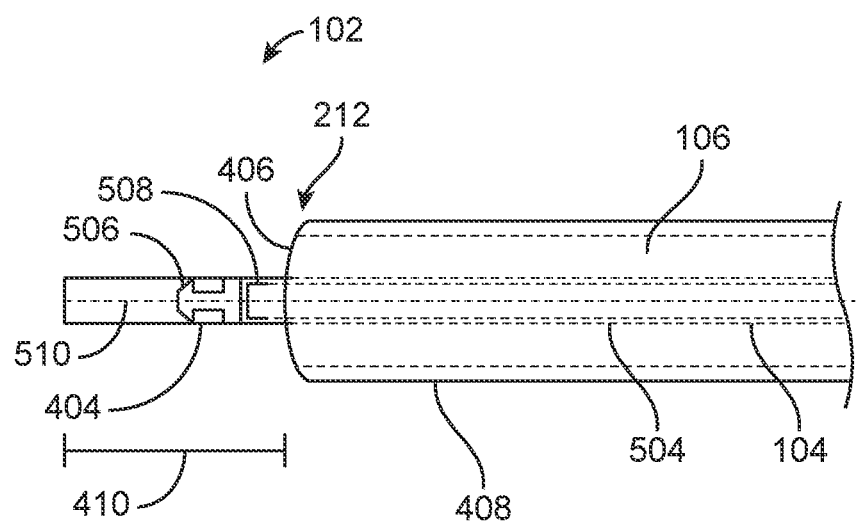
FIG. 5 shows a surgical probe comprising an endoscope comprising a working channel with an implant loaded on an interior of the endoscope, in accordance with some embodiments.

FIG. 5 shows a surgical probe 102 comprising an endoscope 202 comprising a working channel 504 with an implant 506 loaded on an interior of the endoscope 202. The endoscope 202 comprises a curved surface to form an image of the target tissue. The endoscope 202 may comprise a housing 408 that substantially encloses the endoscope 202. In some embodiments, a treatment channel 104 housing such as a tube defines the working channel 504 of the endoscope 202 and extends along an interior of the endoscope 202 and at least to a distal end 212 of the endoscope 202. The distal end of the treatment channel housing 404 may extend a distance 410 from the end of the endoscope 202. The distance 410 can be any suitable distance and can be within a range from about 0 mm to about 10 mm, optionally within a range from about 1 mm to about 5 mm. In some embodiments, the distance 410 is dimensioned for the endoscope 202 to image the distal tip of the treatment channel housing 404, and the endoscope 202 comprises a sufficient depth of field to image the tissue beyond the distal tip, for example within a range from 0.5 mm to 2 mm beyond the distal tip. In some embodiments, the endoscope 202 comprises a curved distal end with the working channel housing 504 and the treatment working channel 504 extending through the end of the endoscope 202. The endoscope 202 may comprise a rod 302 with the treatment channel 104 housing extending along the rod 302. Alternatively, the endoscope 202 may comprise a plurality of optical fibers 402 located around the treatment channel 104 housing.

The surgical probe 102 can be configured in many ways to provide therapy with an implant 506 and perform a procedure as described herein. In some embodiments, the probe 102 comprises a plunger 508 and a stylet 510. The stylet 510 is sized to extend through an inner channel the implant 506 to the target tissue in order to deliver to the implant 506 to the target tissue. In some embodiments, a plunger 508 extends along the working channel 504 to push the implant 506 out the end of the treatment channel 104 and into the tissue. The plunger 508 may comprise an annular shape with an inner diameter sized to receive the stylet 510, and an outer diameter sized to engage the implant 506.

The implant 506 may comprise any suitable implant such as the iStent® or the iStent Inject®, or iStent Inject® W, commercially available from Glaukos, or the Hydrus® commercially available from Ivantis Inc.

In some embodiments, the surgical probe 102 is configured to perform a procedure, such as with a manipulator such as forceps, or with a cutting instrument such as a Trabecutome®, a Kahook blade, or Kahook Dual Blade®. The Trabecutome® may comprise an elongate structure sized and shape to extend along Schlemm's canal and electrodes to cauterize the trabecular meshwork with the elongate structure placed in Schlemm's canal. In some embodiments the elongate structure is fixedly aligned with the one or more indicia of alignment on the hand piece as described herein. The Kahook Dual Blade® may comprise a blade with is sized and shaped to cut along Schlemm's, and the blade can be fixedly aligned with the one or more indicia of alignment of alignment as described herein.

The working channel 504 can be sized to receive the implant 506. For example, the working channel 504 may comprise a diameter within a range from about 0.23 mm to about 0.3 mm, and the stylet 510 may comprise a diameter within a range from about 0.06 mm to about 0.1 mm, for example.

Figure 6:
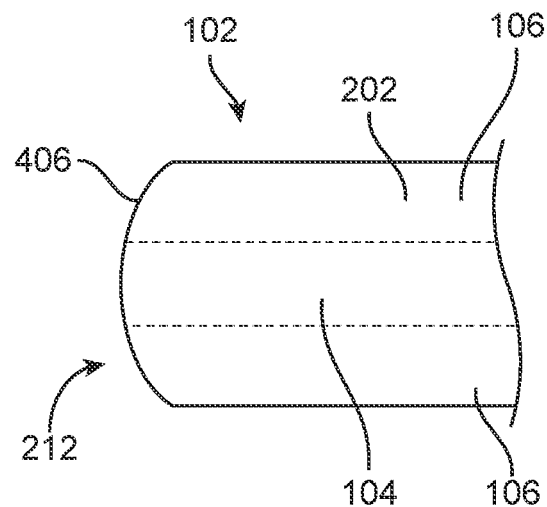
FIG. 6 shows a surgical probe comprising an endoscope with a treatment channel, which ends adjacent to the end of the endoscope, in accordance with some embodiments.

FIG. 6 shows a surgical probe 102 comprising an endoscope 202 with a treatment channel 104, which ends adjacent to the end of the endoscope 202. The treatment channel 104 may comprise an optical fiber 402 or a working channel 504 as described herein. The endoscope 202 comprises a lens 406, and the working channel 504 extends to the end of the endoscope 202 through the lens 406. In some embodiments, the treatment channel 104 comprises an optical fiber 402 with an end surface that extends approximately perpendicular to a long axis of the treatment probe and the optical fiber 402.

Figure 7:
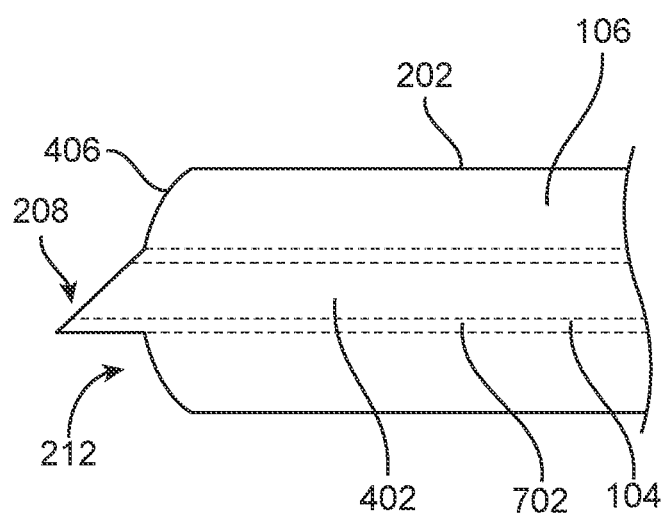
FIG. 7 shows a surgical probe comprising an endoscope with a treatment channel comprising an optical fiber which ends proximate the distal end of the endoscope, in accordance with some embodiments.

FIG. 7 shows a surgical probe 102 comprising an endoscope 202 with a treatment channel 104 comprising an optical fiber 402 which ends proximate the distal end of the endoscope 202. The optical fiber 402 comprises a beveled distal end as described herein. The distal end of the beveled tip of the optical fiber 402 may be within about 0.4 mm of the lens, and the proximal portion of the beveled end may be proximate the curved surface of the lens, for example within about 0.2 mm of the lens. In some embodiments, the optical fiber 402 is at least partially enclosed in a housing such as a tube that extends around the optical fiber 402.

Figure 8:
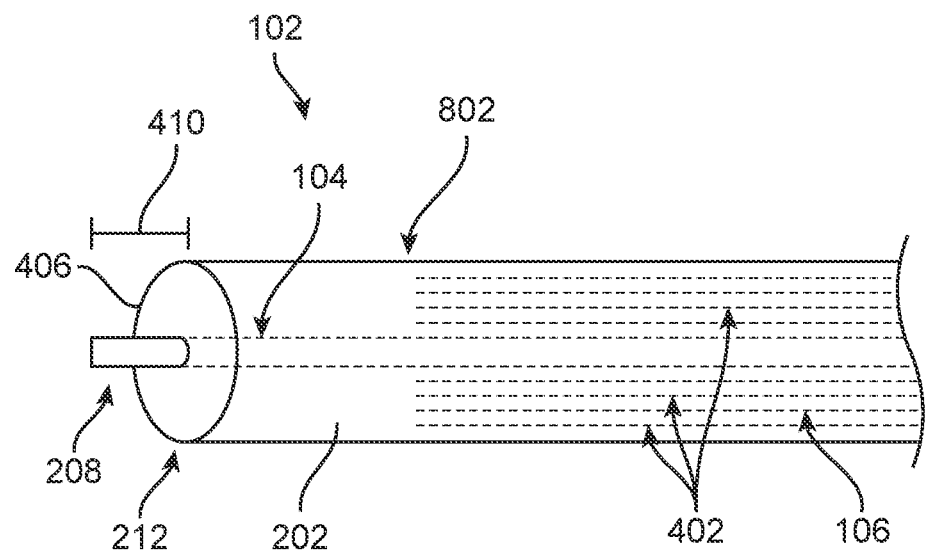
FIG. 8 shows a surgical probe comprising an endoscope comprising a plurality of optical fibers and a lens with a treatment channel extending through the lens, in accordance with some embodiments.

FIG. 8 shows a surgical probe 102 comprising an endoscope 202 comprising a plurality of optical fibers 402 and a lens 406 with a treatment channel 104 extending through the lens 406. The treatment channel 104 may comprise any suitable treatment channel 104, for example as described herein. The treatment ("Tx") channel 104 extends a distance from the tip 212 of the endoscope 202, for example as described herein. The endoscope 202 comprises a lens 406 configured to form an image of the target tissue on the ends of the plurality of optical fibers 402 at an image plane 802. The optical fibers 402 can be coupled to the sensor array 112 in many ways. In some embodiments, the proximal ends of the optical fibers 402 are imaged onto the endoscope 202. Alternatively, the proximal ends of the optical fibers 402 can be coupled to the sensor array 112 as is known to one of ordinary skill in the art. In some embodiments, one or more of the endoscope 202 or the treatment channel 104 comprises a housing as described herein.

Figure 9:
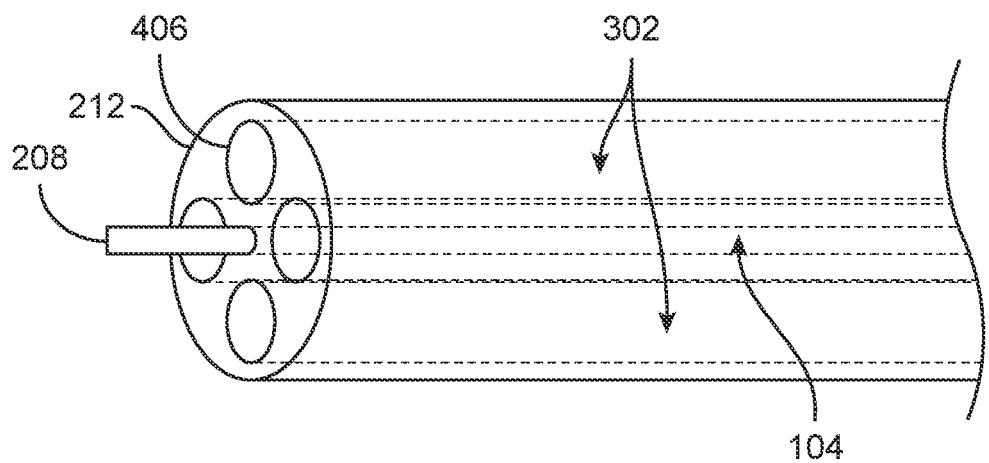
FIG. 9 shows a surgical probe comprising an endoscope comprising a plurality of rods with a treatment channel extending beyond the tip of the endoscope, in accordance with some embodiments.

FIG. 9 shows a surgical probe 102 comprising an endoscope 202 comprising a plurality of rods 302 with a treatment channel 104 extending beyond the tip of the endoscope 202. The plurality of rods 302 may comprise a rod 302 configured to transmit an image toward a proximal end of the rod 302 as described herein, and each of the rods 302 may comprise a mirror 206 with a reflective surface to reflect the image toward one or more sensor arrays 112 as described herein. In some embodiments, each of the rods 302 comprises a mirror 206 coupled to a sensor array 112. In some embodiments, the processor 218 is configured with instructions to combine the images from each of the rods into an image on the display, which image may comprise an image among a series of images.

Figure 10:
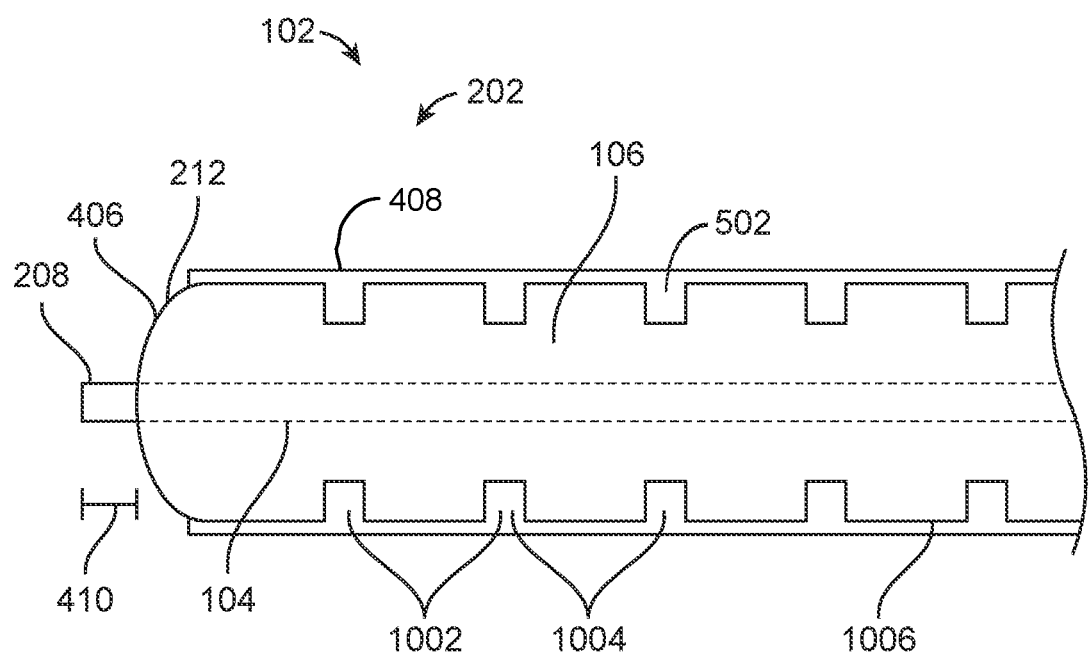
FIG. 10 shows a surgical probe comprising an endoscope comprising a plurality of baffles comprising channels extending into an optically transmissive material, in accordance with some embodiments.

FIG. 10 shows a surgical probe 102 comprising an endoscope 202 comprising a plurality of baffles 1002 comprising grooves 1004 extending into an optically transmissive material. In some embodiments, the end of the endoscope 202 comprises with a treatment channel 104 extending through the lens 406. The treatment channel 104 may comprise any suitable treatment channel 104, for example as described herein. The treatment ("Tx") channel 104 extends a distance 410 from the tip 212 of the endoscope 202, for example as described herein. The lens 406 can be configured in many ways and may comprise a spherical lens or an aspheric lens such as an optimized lens, for example a free form optic, configured to image the target tissue.

In some embodiments, the imaging channel 106 of the endoscope 202 comprises a piece of optically transmissive solid material extending from a proximal portion of the endoscope 202, e.g. near the handpiece 108, to the curved distal surface comprising the lens 406. The piece of solid material may comprise a rod-shaped optically transmissive solid material as described herein. The treatment channel 104 extends along an interior of the rod-shaped solid material as described herein.

The baffles 1002 of the endoscope 202 can be configured in many ways, and in some embodiments comprise a plurality of grooves 1004 extending into the optically transmissive material. In some embodiments, the plurality of baffles 1002 is arranged to decrease internally reflected light. The plurality of grooves 1004 is configured to decrease the transmission of light reflected from an outer reflective surface 1006 of the optically transmissive material. In some embodiments, the grooves 1004 comprise a plurality of separate spaced apart annular grooves configured to decrease the amount of reflected light that reaches the sensor array 112. In some embodiments, the housing 408 comprises a material 502 that extends into the grooves 1004. The housing 408 may comprise a dark material 502 configured to absorb at least some of the light transmitted through the lens 406. While the housing 408 can be configured in many ways, in some embodiments, the housing comprises a plastic material 502 extending into the grooves 1004.

Although reference is made to baffles, in some embodiments the grooves 1004 comprise one or more of a beveled end, a mirror, a Fresnel lens, Fresnel prisms, an etched mirror, a diffractive optic or an echelette.

While the optically transmissive component may comprise any suitable material, in some embodiments the optically transmissive material comprises plastic, such as an injection molded plastic, with the treatment channel 104 extending along an interior of the plastic. Although reference is made to injection molding, the optically transmissive plastic material can be sized and shaped in many ways, for example with one or more of additive manufacturing, e.g. deposition of layers, cutting, polishing, heating or extrusion. The optically transmissive plastic may comprise any suitable plastic, such as one or more of polycarbonate, trivex or CR-39 plastic for embodiments.

The curved lens surface can be manufactured in many ways as described herein. In some embodiments the curve lens comprises a molded lens, such as an injection molded lens, for example. Alternatively or in combination the lens 406 may comprise a ground surface, such as diamond turning or polishing as is known in the field of optometric lens design, for example.

Although reference is made to a single piece of optically transmissive material, in some embodiments, a lens 406 is located on the end of the rod 302, in which the lens 406 comprises a separate component coupled to the rod 302, e.g. bonded to the rod. Alternatively or in combination, the lens 406 may be held place and coupled to the rod 302, for example within a tube extending from the rod 302.

The treatment channel 104 of the endoscope rod 302 can be configured in many ways as described herein. In some embodiments, the treatment channel 104 is bored through the endoscope rod 302, and a housing 408 such as a sheath inserted into the channel so that the tip 208 extends a suitable distance from the end of the curved surface of the endoscope tip 212 as described herein.

In some embodiments, the rod 302 comprises an injection molded component with the grooves 1004 formed in the injection molded part. In some embodiments, the injection molded part is formed with the treatment channel 104, e.g. the housing placed in the injection mold prior to molding the optically transmissive rod 302, and the housing 408 and molded rod removed from the mold. Alternatively the treatment channel 104 can be bored into the injection molded part. The outer housing 408 that extends into the baffles 1002 can be formed in many ways, and may comprise an injection molded part, and may be injection molded over the optically transmissive component, for example. Alternatively, the housing 408 may be bonded to the endoscope rod 302 comprising the optically transmissive material.

Figure 11A:
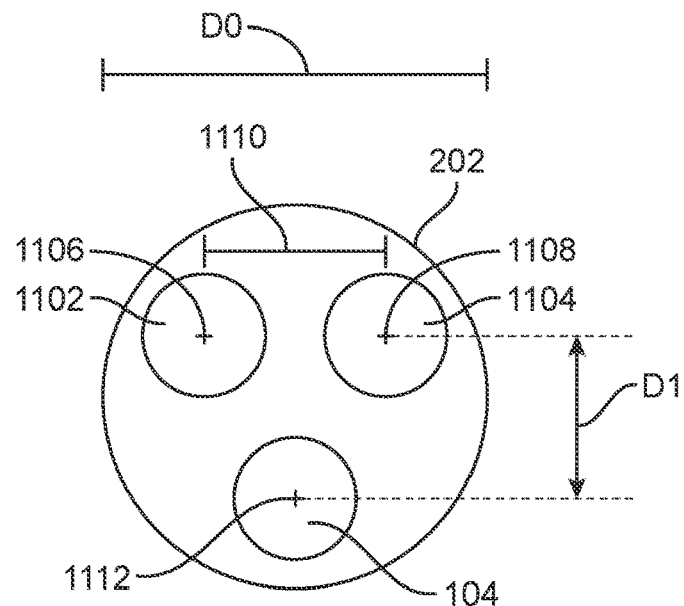
FIG. 11A shows an end view of a stereoscopic endoscope, in accordance with some embodiments.

FIG. 11A shows an end view of a stereoscopic endoscope 202, in accordance with some embodiments. The endoscope 202 comprises a first lens 1102, a second lens 1104 and a treatment channel 104 as described herein. The first lens 1102 comprises a first center 1106 and the second lens 1104 comprises a center 1108. A distance 1110 extends between the first center 1106 of the first lens 1102 and the second center 1108 of the second lens 1104. A distance D1 extends between centers of the lenses 1102, 1104, and the treatment channel center 1112. The inter lens distance IPD 1110 and distance D1 from the lens centers to the working channel center 1112 can be arranged to provide stereoscopic vision of the distal end of the probe 102 as described herein.

Figure 11B:
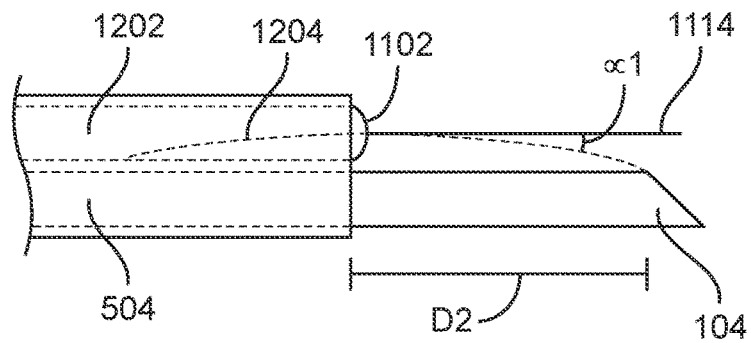
FIG. 11B shows a side view of the stereoscopic endoscope as in FIG. 11A, in accordance with some embodiments.

FIG. 11B shows a side view of the stereoscopic endoscope 202 as in FIG. 11A, in accordance with some embodiments. The stereoscope endoscope 202 comprises first optical channel 1202 associated with lens 1102. The first optical channel 1202 transmits light energy from the lens 1102 along an optical path to the sensor array 112 as described herein. The first optical channel 1202 may comprise a rod or a bundle of optical fibers 402 as described herein. The first optical channel 1202 comprises an axis that may extend substantially parallel to the endoscope 202. A ray 1204 of light is shown travelling from the endoscope 202 tip to, through a center of lens 1102 and substantially parallel along the first optical channel 1202 within the endoscope 202. The ray 1204 may be deflected by an angle $\alpha 1$ with respect to the axis when entering the lens 1102, such that the ray 1204 travels substantially parallel to the optical axis of the first optical channel 1202, for example substantially parallel to within about 10 degrees.

Figure 11C:
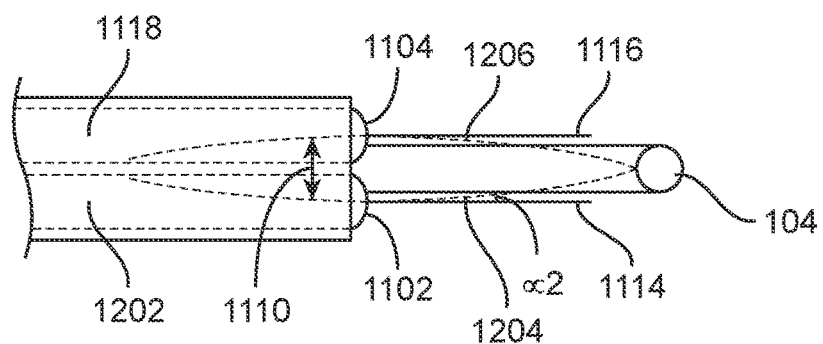
FIG. 11C shows a top view of the stereoscopic endoscope as in FIGS. 11A and 11B, in accordance with some embodiments.

FIG. 11C shows a top view of the stereoscopic endoscope 202 as in FIGS. 11A and B, in accordance with some embodiments. The center of the first lens 1102 and center of the second lens 1104 are separated by a distance 1110. The ray 1204 is shown deflected by a second angle $\alpha 2$ with respect to the elongate axis. The ray 1206 is shown with similar deflections with respect to the second lens 1104. The ray 1206 may be deflected similarly to ray 1204, for example with deflections at first angle $\alpha 1$ and second angle $\alpha 2$ with respect to the elongate axis, in order to provide stereoscopic images of the tip of the treatment channel 104 to the image sensor 112. Although reference is made to providing stereoscopic images of the tip of the treatment channel 104, the stereoscopic images may comprise images of any suitable object such as the tip of an optical fiber 402 or a tip of an implant 506 as described herein.

The first lens 1102 and the second lens 1104 can be configured in many ways to provide the appropriate deflections of the rays from the object near the tip of the treatment channel 104, such as an implant 506 or optical fiber 402. In some embodiments, the first lens 1102 and the second lens 1104 each comprise a prism to provide the corresponding deflections. In some embodiments, the first lens 1102 and the second lens 1104 comprises separate portions of an objective lens, in which each of the portions is defined with an aperture to provide appropriate amounts of prism.

The stereoscopic endoscope 202 can be configured in many ways to provide depth perception to the user. The distance D2 may comprise a distance from the distal tip of one or more lenses 216 to a distal tip of the working channel 504. In some embodiments, the distance D2 is within a range from about 2 mm to about 6 mm, e.g. about 4 mm, for example. In some embodiments, the first angle $\alpha 1$ is within a range from 1 to 5 degrees and the second angle $\alpha 2$ is within a range from 15 degrees to 45 degrees, e.g. about 30 degrees. The field of view of each of lenses 1102, 1104 can be within a range from about 35 to 75 degrees, e.g. about 60 degrees. The overall diameter DO of the endoscope 202 can be within a range from about 0.5 mm to about 2 mm, for example within a range from 0.75 to 1.5 mm, e.g. about 1 mm in diameter. Although reference is made to a diameter, the endoscope 202 may comprise non-circular cross-sectional shapes, e.g. elliptical, in which the average distance across the cross-section corresponds approximately to the diameter.

The lenses 1102, 1104 may comprise any suitable lenses 216. In some embodiments, lenses 1102, 1104 comprise gradient index ("GRIN") lenses, which may comprise rods of suitable length of GRIN optical fiber, for example. Alternatively or in combination, lenses 1102, 1104 may comprise plastic material as described herein. Each of lenses 1102, 1104 may comprise any suitable lens 406 as described herein, such as one or more of a Fresnel lens, an etched mirror, a diffractive optic, a holographic optic, a Fresnel zone plate, a GRIN lens or an echelette, and combinations thereof.

Although the endoscope 202 is shown combined with a treatment probe in FIGS. 1 to 11C, in some embodiments, the endoscope 202 can be configured without the treatment channel 104 and provided separately from the surgical probe. In some embodiments, the separate endoscope 202 comprises a single viewing channel as described herein. Alternatively, the endoscope 202 may comprise a plurality of viewing channels, e.g. a first viewing channel and a second viewing channel, in order to image the probe with stereoscopic vision. The endoscope 202 can be used to view a surgical procedure performed with the treatment probe.

Figure 12:
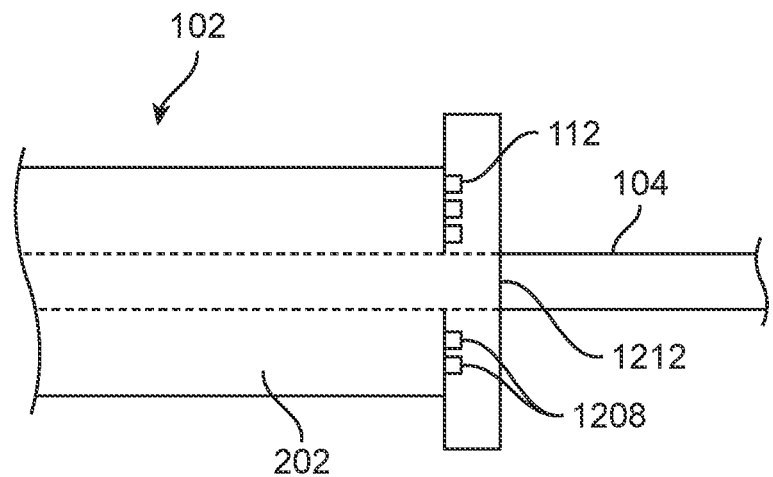
FIG. 12 shows a surgical probe comprising a plurality of sensor elements distributed around a treatment channel, in accordance with some embodiments.

FIG. 12 shows a surgical probe 102 comprising a plurality of sensor elements 1208 distributed around a treatment channel 104. The sensor elements 1208 may be any suitable sensor elements, such as those shown and described in relation to FIG. 1. The treatment channel 104 may comprise any suitable treatment channel 104 as described herein, e.g. a working channel 504 to delivery an implant 506 or a channel comprising an optical fiber 402. The plurality of sensor elements 1208 can be configured in many ways, and may comprise sensors of an array 1210, e.g. pixels. In some embodiments, the sensor array 112 comprises an aperture 1212 formed between pixels of the array 112, such that the treatment channel 104 extends through the array 112. Alternatively or in combination, the array 112 may comprises individual sensor elements 1208 supported with the endoscope 202, which are distributed around the treatment channel 104.

Figure 13:
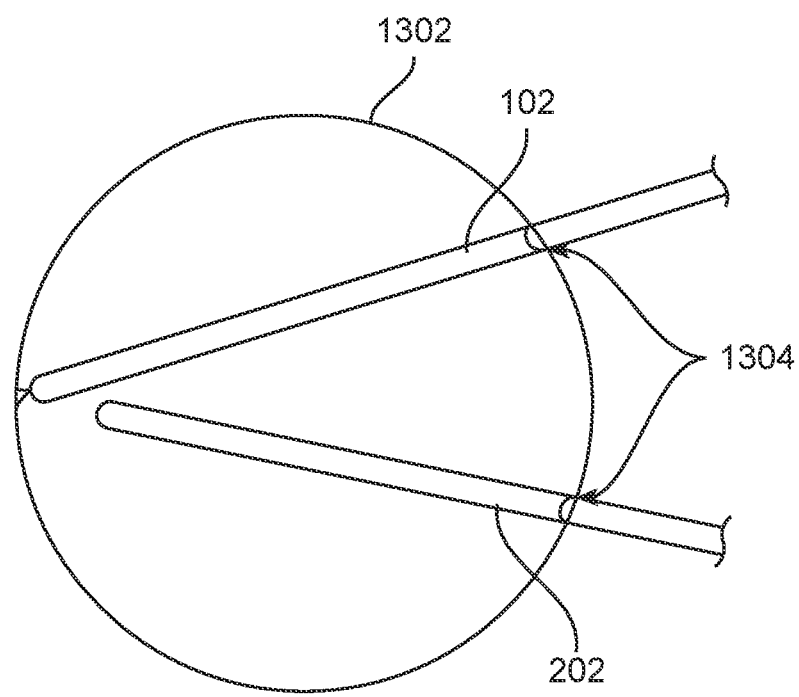
FIG. 13 shows an eye with a plurality of incisions through which a treatment probe and an endoscope have been inserted, in accordance with some embodiments.

FIG. 13 shows an eye 1302 with a plurality of incisions 1304 through which a surgical probe (Tx probe) 102 and an endoscope 202 have been inserted, in accordance with some embodiments. The surgical probe 102 comprises a treatment channel 104 as described herein. The endoscope 202 comprises an endoscope 202 as described herein, such as a stereoscopic endoscope, for example. The endoscope 202 can be used to view the surgical probe 102, and interaction of the surgical probe 102 with tissue.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A surgical instrument comprising: an endoscope to image a surgical site; a treatment channel extending along an interior of the endoscope, wherein the treatment channel comprises one or more of an optical fiber to deliver light energy or a working channel configured to deliver an implant, manipulate an implant or perform a procedure.

Clause 2. The surgical instrument of clause 1, wherein the endoscope comprises a lens and the treatment channel extends through the lens.

Clause 3. The surgical instrument of clause 2, wherein the treatment channel extends coaxially through the lens.

Clause 4. The surgical instrument of clause 3, the lens comprises an optical axis and the treatment channel comprises a treatment channel axis extending along an elongate dimension of the treatment channel and wherein the optical axis extends coaxially with the treatment channel axis.

Clause 5. The surgical instrument of clause 1, wherein the treatment channel extends beyond a distal end of an optical fiber in order to illuminate a distal end of the treatment channel with light emitted from the distal end of the optical fiber.

Clause 6. The surgical instrument of clause 5, wherein the optical fiber comprises an optical fiber of the endoscope and the optical fiber of the endoscope is configured to image the distal end of the treatment channel.

Clause 7. The surgical instrument of clause 5, wherein the endoscope comprises a second optical fiber and the second optical fiber is configured to image the distal end of the treatment channel while the first optical fiber illuminates the treatment channel and optionally wherein the optical fiber comprises a first optical fiber located outside the endoscope.

Clause 8. The surgical instrument of clause 1, wherein the endoscope comprises a rod, the rod comprising a curved end and the treatment channel.

Clause 9. The surgical instrument of clause 8, wherein the curved end comprises a lens to form an image of the surgical site.

Clause 10. The surgical instrument of clause 8, wherein the rod comprises a beveled proximal end with the treatment channel extending therethrough, the beveled proximal end comprising a reflective surface to reflect light from the curved end toward a sensor array.

Clause 11. The surgical instrument of clause 9, wherein the rod comprises an elongate central axis and wherein the working channel extends along the elongate central axis.

Clause 12. The surgical instrument of clause 10, wherein the working channel comprises an elongate central axis and wherein the elongate axis of the working channel extends coaxially with the elongate central axis of the rod.

Clause 13. The surgical instrument of clause 1, wherein the endoscope comprises a housing at least partially enclosing the endoscope and wherein the treatment channel comprises a tube.

Clause 14. The surgical instrument of clause 1, wherein the treatment channel comprises an optical fiber.

Clause 15. The surgical instrument of clause 1, wherein the treatment channel comprises a housing enclosing an optical fiber.

Clause 16. The surgical instrument of clause 1, wherein the endoscope comprises an optical fiber extending to one or more of a beveled end, a mirror, a Fresnel lens, Fresnel prisms, an etched mirror, a diffractive optic or an echelette.

Clause 17. The surgical instrument of clause 1, wherein the treatment channel comprises an optical fiber extending to one or more of a beveled end, a mirror, a Fresnel lens, Fresnel prisms, an etched mirror, a diffractive optic or an echelette.

Clause 18. The surgical instrument of clause 1, wherein the optical fiber comprises a GRIN lens.

Clause 19. The surgical instrument of clause 1, wherein the treatment channel comprises a housing enclosing a working channel, the working channel configured to deliver an implant, manipulate an implant or perform a procedure.

Clause 20. The surgical instrument of clause 1, wherein the treatment channel comprises a housing extending to a tip located a distance from the end of the endoscope.

Clause 21. The surgical instrument of clause 19, wherein the distance is dimensioned to form an image of the tip of the housing and optionally wherein the endoscope comprises a depth of field sufficient to image the tip and tissue distal to the tip in order to guide the tip to the tissue.

Clause 22. The surgical instrument of clause 1, wherein the treatment channel comprises a housing extending to a tip located adjacent the end of the endoscope.

Clause 23. The surgical instrument of clause 1, wherein the endoscope comprises a one or more optical fibers arranged in relation the treatment channel.

Clause 24. The surgical instrument of clause 1, wherein the endoscope comprises a plurality of optical fibers arranged around the treatment channel.

Clause 25. The surgical instrument of clause 1, wherein the endoscope comprises one or more rods arranged in relation to the treatment channel.

Clause 26. The surgical instrument of clause 1, wherein the endoscope comprises a plurality of rods arranged around the treatment channel.

Clause 27. The surgical instrument of any one of the preceding clauses, wherein the endoscope comprises a rod comprising a plurality of baffles.

Clause 28. The surgical instrument of any one of the preceding clauses, wherein the endoscope comprises a plurality of optical structures provide an image to the sensor array, the plurality of optical structures comprising one or more of a Fresnel lens, an etched mirror, a diffractive optic, a holographic optic, a Fresnel zone plate, a GRIN lens, or an echelette.

Clause 29. The surgical instrument of any one of the preceding clauses, wherein the endoscope comprises an injection molded optically transmissive material comprising a plurality of baffles to decrease internally reflected light.

Clause 30. The surgical instrument of any one of the preceding clauses, wherein the treatment channel is located coaxially with a lens of the endoscope to decrease parallax of an image of a tip of the treatment channel extending beyond the lens.

Clause 31. A stereoscopic surgical instrument comprising: an endoscope to image a surgical site with stereoscopic vision of the surgical site; a treatment channel extending along an interior of the endoscope, wherein the treatment channel comprises one or more of an optical fiber to deliver light energy or a working channel configured to deliver an implant, manipulate an implant, or perform a procedure.

Clause 32. The stereoscopic surgical instrument of clause 30, wherein the endoscope comprises a first aperture corresponding to vision of a first eye and a second aperture corresponding to vision of a second eye, and wherein the treatment channel is located at least partially between the first aperture and the second aperture.

Clause 33. The stereoscopic surgical instrument of clause 30, wherein the endoscope comprises a first aperture corresponding to vision of a first eye on a first side of the treatment channel and a second aperture corresponding to vision of a second eye on a second side of the treatment channel and wherein a rotational orientation of the first aperture and the second aperture is fixed with respect to the treatment channel.

Clause 34. The stereoscopic surgical instrument of clause 32, wherein the treatment channel comprises an optical fiber or an implant, and wherein a rotational orientation of the optical fiber or the implant is fixed within the treatment channel in relation to the first aperture and the second aperture.

Clause 35. The stereoscopic surgical instrument of clause 30, wherein the treatment channel extends beyond one or more distal lenses of the endoscope and the one or more lenses is configured to image one or more of an optical fiber or an implant located near the end of the treatment channel with stereoscopic vision.

Clause 36. The stereoscopic surgical instrument of clause 30, wherein the endoscope comprises a first optical channel corresponding to vision of a first eye and a second optical channel corresponding to vision of a second eye, and wherein the treatment channel, the first optical channel and the second optical channel are arranged to view, with stereoscopic vision, tissue beyond a distal end of the endoscope and the distal end of the probe with depth perception.

Clause 37. The stereoscopic surgical instrument of clause 30, wherein the endoscope comprises a first optical channel corresponding to vision of a first eye and a second optical channel corresponding to vision of a second eye, and wherein the treatment channel, the first optical channel and the second optical channel are arranged to view, with stereoscopic vision, one or more of a distal end of an implant, a distal end of an optical fiber, or a distal end of a stylet with stereoscopic vision.

Clause 38. The stereoscopic surgical instrument of clause 36, wherein the first optical channel comprises a first rod and the second optical channel comprises a second rod.

Clause 39. The surgical instrument of any one of clauses 30 to 37, wherein the treatment channel is located eccentrically with respect to one or more lenses of the endoscope to provide parallax and stereoscopic images of tip of the treatment channel extending beyond the one or more lenses.

Clause 40. A surgical instrument comprising: an endoscopic probe to form an image of a treatment site; and a treatment probe to provide a treatment to the treatment site.

Clause 41. A method of treating an eye, the method comprising: inserting an endoscope probe into the eye through a first opening in a wall of the eye; inserting a treatment probe into the eye through a second opening in the wall of the eye; and treating the eye with the treatment probe while the endoscopic probe images tissue and a distal end of the treatment probe.

Clause 42. A surgical instrument, stereoscopic surgical instrument or method of any one of the preceding clauses, further comprising a connector to couple a sensor array to the endoscope and optionally wherein the connector is configured to couple the sensor array to the endoscope with a fixed angular orientation.

Clause 43. The surgical instrument, stereoscopic instrument, or method of any one of the preceding clauses, wherein one or more of the endoscope or the treatment channel is configured to illuminate the distal end of the probe and tissue near the distal end of the probe.

Clause 44. The surgical instrument, stereoscopic instrument, or method of clause 42, wherein the treatment channel comprises an optical fiber configured to illuminate the distal end and the tissue.

Clause 45. The surgical instrument, stereoscopic instrument, or method of clause 42, wherein the treatment channel extends beyond a distal end of an optical fiber in order to illuminate a distal end of the treatment channel with light emitted from the distal end of the optical fiber.

Clause 46. The surgical instrument, stereoscopic instrument, or method of clause 42, wherein the endoscope comprises one or more optical fibers configured to illuminate the distal end and the tissue.

Clause 47. The surgical instrument, stereoscopic instrument, or method of clause 45, wherein an imaging channel of the endoscope comprises the one or more optical fibers to illuminate the distal end and the tissue.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A surgical instrument to treat tissue of an eye, the surgical instrument comprising:
   an endoscope to image a surgical site of the eye; and
   a treatment channel extending along an interior of the endoscope, wherein the treatment channel comprises a treatment optical fiber to deliver light energy to the tissue;
   wherein the endoscope comprises a distal lens that defines a central optical axis and the treatment channel extends through the distal lens along the central optical axis, the distal lens configured to substantially collimate light from the tissue to form an image of the tissue within the endoscope.

2. The surgical instrument of claim 1, wherein the treatment optical fiber extends beyond a distal end of an illumination optical fiber in order to illuminate a distal end of the treatment channel with light emitted from the distal end of the illumination optical fiber.

3. The surgical instrument of claim 2, wherein the illumination optical fiber comprises an optical fiber of the endoscope and the optical fiber of the endoscope is configured to image the distal end of the treatment optical fiber.

4. The surgical instrument of claim 2, wherein the endoscope comprises a second optical fiber and the second optical fiber is configured to image the distal end of the treatment optical fiber.

5. The surgical instrument of claim 1, wherein the endoscope comprises a rod, the rod comprising a curved end and the treatment optical fiber.

6. The surgical instrument of claim 5, wherein the curved end comprises a lens to form an image of the tissue.

7. The surgical instrument of claim 5, wherein the rod comprises a beveled proximal end with the treatment optical fiber extending therethrough, the beveled proximal end comprising a reflective surface to reflect light from the curved end toward a sensor array.

8. The surgical instrument of claim 7, wherein the rod comprises an elongate central axis and wherein the treatment optical fiber extends along the elongate central axis.

9. The surgical instrument of claim 8, wherein the treatment optical fiber comprises an elongate central axis and wherein the elongate central axis of the treatment optical fiber extends coaxially with the elongate central axis of the rod.

10. The surgical instrument of claim 1, wherein the endoscope comprises a housing at least partially enclosing the endoscope and wherein the endoscope comprises a tube sized to receive the treatment optical fiber.

11. The surgical instrument of claim 1, wherein a housing encloses the treatment optical fiber.

12. The surgical instrument of claim 1, wherein the endoscope comprises an imaging optical fiber extending to one or more of a beveled end, a mirror, a Fresnel lens, Fresnel prisms, an etched mirror, a diffractive optic or an echelette.

13. The surgical instrument of claim 1, wherein the treatment optical fiber extends to one or more of a beveled end, a mirror, a Fresnel lens, Fresnel prisms, an etched mirror, a diffractive optic or an echelette.

14. The surgical instrument of claim 1, wherein an imaging optical fiber comprises a GRIN lens.

15. The surgical instrument of claim 1, wherein the treatment optical fiber comprises a housing extending to a tip located a distance from the end of the endoscope.

16. The surgical instrument of claim 15, wherein the distance is dimensioned to form an image of the tip of the housing.

17. The surgical instrument of claim 16, wherein the endoscope comprises a depth of field sufficient to image the tip of the treatment optical fiber and the tissue distal to the tip of the treatment optical fiber in order to guide the tip to the tissue.

18. The surgical instrument of claim 15, wherein the distance is dimensioned to form an image of the tip of the treatment optical fiber.

19. The surgical instrument of claim 1, wherein the endoscope comprises a rod comprising a plurality of baffles.

20. The surgical instrument of claim 1, wherein the endoscope comprises a plurality of optical structures provide an image to a sensor array, the plurality of optical structures comprising one or more of a Fresnel lens, an etched mirror, a diffractive optic, a holographic optic, a Fresnel zone plate, a GRIN lens, or an echelette.

21. The surgical instrument of claim 1, wherein the treatment optical fiber extends coaxially with the distal lens of the endoscope to decrease parallax of an image of a tip of the treatment optical fiber extending beyond the distal lens.

22. The surgical instrument of claim 1, wherein the treatment optical fiber extends beyond the distal lens of the endoscope and the distal lens is configured to image the treatment optical fiber.

* * * * *